United States Patent [19]

Ishida et al.

[11] Patent Number: 5,491,080
[45] Date of Patent: Feb. 13, 1996

[54] PLANTS RESISTANT AGAINST PLURAL VIRUSES AND METHOD FOR PRODUCING THEM USING AS RNASE GENES

[75] Inventors: Isao Ishida, Yokohama; Yoshimi Okada, Matsudo, both of Japan

[73] Assignee: Kirin Beer Kabushiki Kaisha, Tokyo, Japan

[21] Appl. No.: 157,189

[22] PCT Filed: Apr. 16, 1993

[86] PCT No.: PCT/JP93/00494

§ 371 Date: Feb. 17, 1994

§ 102(e) Date: Feb. 17, 1994

[87] PCT Pub. No.: WO93/20686

PCT Pub. Date: Oct. 28, 1993

[30] Foreign Application Priority Data

Apr. 17, 1992 [JP] Japan ..................... 4-122837
Dec. 2, 1992 [JP] Japan ..................... 4-349791

[51] Int. Cl.[6] ................ C12N 15/00; A01H 1/04
[52] U.S. Cl. ............. 435/172.3; 435/69.1; 435/199; 435/70.1; 800/205; 800/DIG. 43
[58] Field of Search ................ 800/205, DIG. 43; 435/172.3, 69.1, 199, 70.1

[56] References Cited

U.S. PATENT DOCUMENTS

| | | | |
|---|---|---|---|
| 4,990,498 | 2/1991 | Suhadolnik | 514/47 |
| 5,254,678 | 10/1993 | Haseloff et al. | 536/23.2 |

FOREIGN PATENT DOCUMENTS

| | | |
|---|---|---|
| 0298918 | 1/1989 | European Pat. Off. |
| 0360257 | 3/1990 | European Pat. Off. |
| 0421376 | 4/1991 | European Pat. Off. |
| 0428881 | 5/1991 | European Pat. Off. |
| 0479180 | 4/1992 | European Pat. Off. |
| 4016483 | 11/1991 | Germany. |

OTHER PUBLICATIONS

March, P. E., "The DNA Sequence of the Gene (rnc) Encoding Ribonuclease III of *Escherichia coli*", *Nucleic Acids Research*, vol. 13, (1985).

Iino, Y. et al., "*S.pombe pac1+*, Whose Overexpression Inhibits Sexual Development, Encodes a Ribonuclease III–like RNase", *The EMBO Journal*, vol. 10, pp. 221–226 (1991).

Kaniewski, W., "Field Resistance of Transgenic Russet Burbank Potato to Effects of Infection by Potato Virus X and Potato Virus Y", *Bio Technology*, vol. 8 (Aug. 1990).

Grumet, R., "Genetically Engineered Plant Virus Resistance", *HortScience*, vol. 25(5), pp. 508–513 (May 1990).

Gadani, F. et al., "Genetic Engineering of Plants for Virus Resistance", *Archives of Virology*, vol. 115, pp. 1–21 (1990).

Gergerich, R. C. et al., "The Enzymatic Function of Ribonuclease Determines Plant Virus Transmission by Leaf–Feeding Beetles", *Phytopathology*, vol. 78, pp. 270–272 (Abstract) (1988).

Kremmer, E., "Murine Anti–Mouse T Cell Monoclonal Antibodies Elicit Anti–Antibodies in Mice: Intra–Species Immunization Model for Estimating Potential Patient Sensitization Against Humanized Anti–T Cell Antibodies", *Eur. J. Immunol.*, vol. 23, pp. 1017–1022 (1993).

Barton et al (1987) Plant Physiol 85:1103–1109.

Stark et al (1989) Biotechnology 7:1257–62.

*Primary Examiner*—David T. Fox
*Assistant Examiner*—Elizabeth F. McElwain
*Attorney, Agent, or Firm*—Foley & Lardner

[57] ABSTRACT

This invention relates to a method for producing a plant having resistance against RNA viruses by integrating a DNA sequence, which encodes a protein having an enzyme activity specifically breaking down a double-strand RNA, into a chromosome of a plant and making the DNA sequence express in the plant cells; and a plant having resistance against RNA viruses obtained according to the above method.

A plant according to the present invention has resistance against plural RNA viruses.

12 Claims, 17 Drawing Sheets

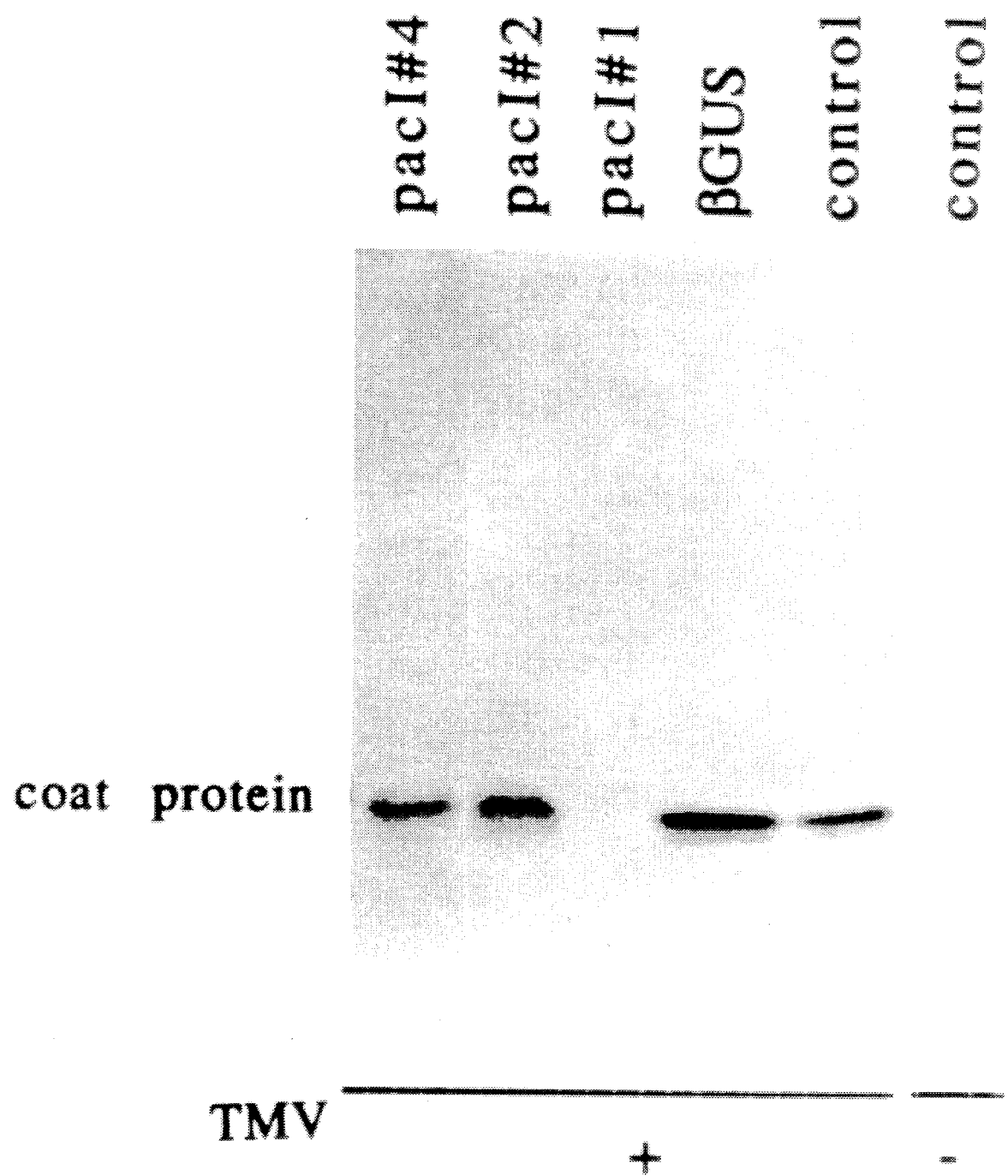

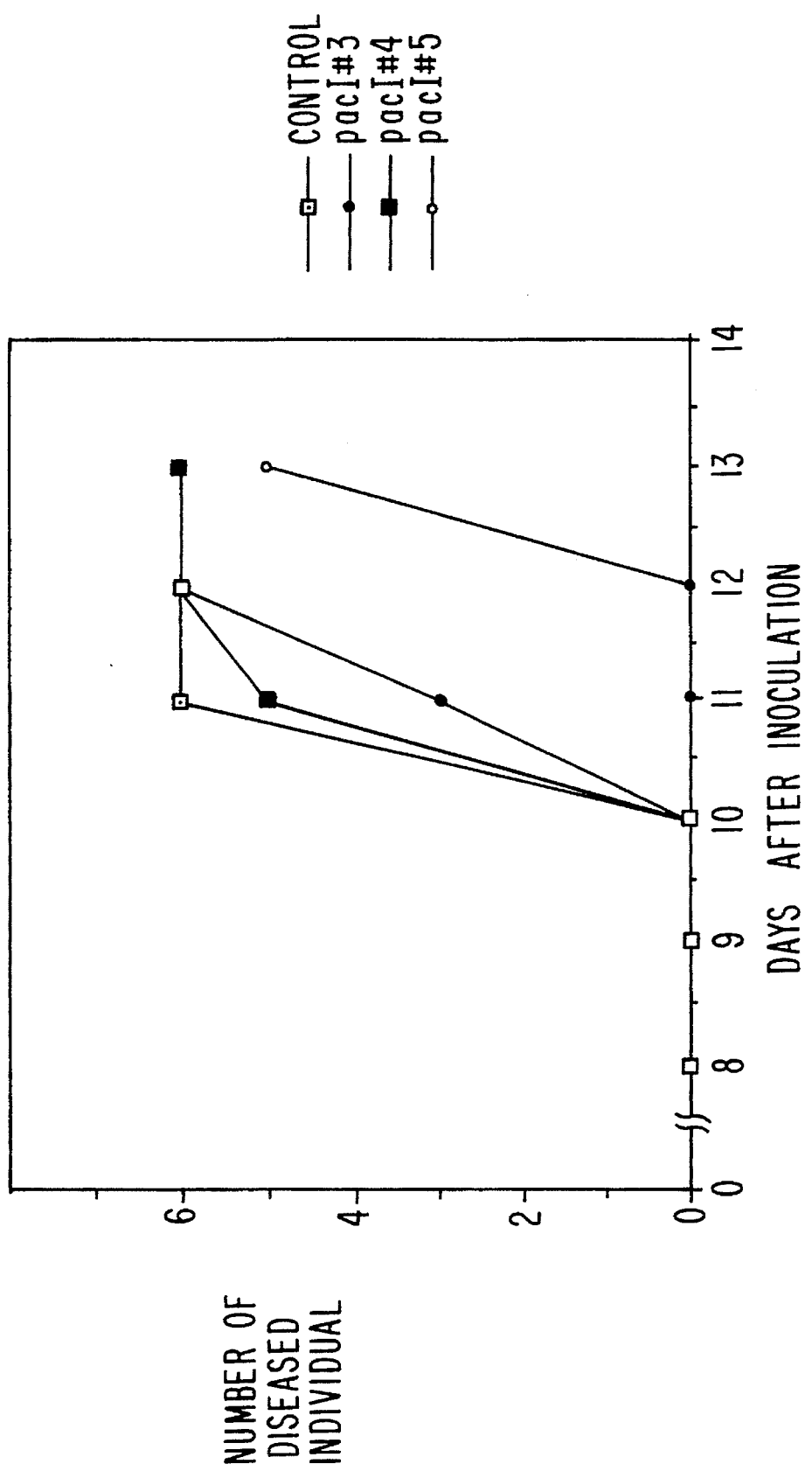

FIG. 14A

```
        10         20         30         40         50         60
ccgaattccA TGAACCCAAT CbTTATCAAC AGGCTTCAAA GGAAGCTTGG ATACACCTTC
ggcttaaggT ACTTGGGTTA GCAATAGTTG TCCGAAGTTT CCTTCGAACC TATGTGGAAG
  EcoRI 70         80         90        100        110        120
AACCACCAAG AGCTTCTTCA ACAAGCTCTT ACCCACAGGT CTGCTTCTTC TAAGCACAAC
TTGGTGGTTC TCGAAGAAGT TGTTCGAGAA TGGGTGTCCA GACGAAGAAG ATTCGTGTTG 130        140        150        160        170        180
GAGAGGCTTG AGTTCCTTGG AGACTCTATC CTTTCTTACG TTATCGCTAA CGCTCTTTAC
CTCTCCGAAC TCAAGGAACC TCTGAGATAG GAAAGAATGC AATAGCGATT GCGAGAAATG 190        200        210        220        230        240
CACAGGTTCC CAAGGGTTGA CGAGGGAGAC ATGTCTAGGA TGAGGGCTAC CCTTGTTAGG
GTGTCCAAGG GTTCCCAACT GCTCCCTCTG TACAGATCCT ACTCCCGATG GGAACAATCC 250        260        270        280        290        300
GGAAACACCC TTGCTGAGCT TGCTAGGGAG TTCGAGCTTG GAGAGTGCCT TAGGCTTGGA
CCTTTGTGGG AACGACTCGA ACGATCCCTC AAGCTCGAAC CTCTCACGGA ATCCGAACCT 310        320        330        340        350        360
CCAGGAGAGC TTAAGTCTGG AGGATTCAGG AGGGAGTCTA TCCTTGCTGA CACCGTTGAG
GGTCCTCTCG AATTCAGACC TCCTAAGTCC TCCCTCAGAT AGGAACGACT GTGGCAACTC
```

FIG. 14B

```
          370        380        390        400        410        420
     GCTCTTATCG GAGGAGTTTT CCTTGACTCT GACATCCAAA CCGTTGAGAA GCTTATCCTT
     CGAGAATAGC CTCCTCAAAA GGAACTGAGA CTGTAGGTTT GGCAACTCTT CGAATAGGAA 430        440        450        460        470        480
     AACTGGTACC AAACCAGGCT TGACGAGATC TCTCCAGGAG ACAAGCAAAA GGACCCAAAG
     TTGACCATGG TTTGGTCCGA ACTGCTCTAG AGAGGTCCTC TGTTCGTTTT CCTGGGTTTC 490        500        510        520        530        540
     ACCAGGCTTC AAGAGTACCT TCAAGGAAGG CACCTTCCAC TTCCAACCTA CCTTGTTGTT
     TGGTCCGAAG TTCTCATGGA AGTTCCTTCC GTGGAAGGTG AAGGTTGGAT GGAACAACAA 550        560        570        580        590        600
     CAAGTTAGGG GAGAGGCTCA CGACCAAGAG TTCACCATCC ACTGCCAAGT TTCTGGACTT
     GTTCAATCCC CTCTCCGAGT GCTGGTTCTC AAGTGGTAGG TGACGGTTCA AAGACCTGAA 610        620        630        640        650        660
     TCTGAGCCAG TTGTTGGAAC CGGATCTTCT AGGAGGAAGG CTGAGCAAGC TGCTGCTGAA
     AGACTCGGTC AACAACCTTG GCCTAGAAGA TCCTCCTTCC GACTCGTTCG ACGACGACTT 670        680        690        700        710        720
     CAAGCTCTTA AGAAGCTTGA GCTTGAAtaa ttttagcag agtcgacgg. ..........
     GTTCGAGAAT TCTTCGAACT CGAACTTatt aaaatcgtc tcagctgcc ..........
                                                      Sall
```

FIG. 16A (CONTROL)
FIG. 16B (HOMO)
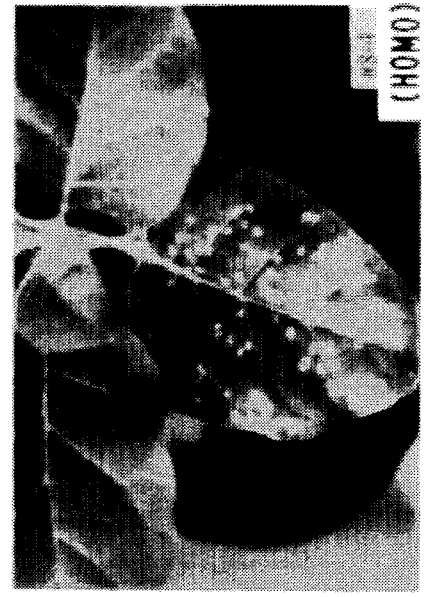
FIG. 16C (HETERO)
FIG. 16D (HOMO)

PLANTS RESISTANT AGAINST PLURAL VIRUSES AND METHOD FOR PRODUCING THEM USING AS RNASE GENES

TECHNICAL FIELD

This invention relates to a technique for producing a plant resistant against RNA viruses by means of genetic recombination technology. More specifically, this invention relates to a method for producing a plant resistant against plural RNA viruses by integrating a DNA sequence, which encodes a protein having an enzyme activity specifically breaking down a double-strand RNA, into a chromosome of a plant and making the DNA sequence express in the plant cells, and a plant resistant against plural viruses obtained according to the above method.

TECHNICAL BACKGROUND

Viral infection is one of big sources of stress for plants. It is not uncommon that damages by viral diseases influence and move the habitat of crops and a variety is renewed. However, there is no effective drug which directly act upon viruses at present, so that the control of such viruses is dependent solely upon indirect means. Although it is one of important purposes of breeding to give viral resistance to a crop, there are many cases where any resistant genetic resource cannot be found in wild species or relative species which can be bred with the crop. In such a case, a virus resistant variety could not have bred according to the conventional breeding techniques such as cross-breeding and the like.

As a method for covering up such faults of the conventional breeding techniques, methods for giving virus resistance to a plant by means of genetic recombination technology have been developed recently. When the genetic recombination technology is available, not only the gene transfer which goes over the wall of the above-mentioned conventional cross-breeding becomes possible but also it is possible to introduce virus resistance directly into an existing variety which is agronomically important.

As regard as giving virus resistance to a plant by means of genetic recombination technology, methods for making virus-derived genes (a gene encoding the coat protein of a virus, cDNA of a satellite RNA) express in a plant have been reported [e.g., *HortScience*, vol. 25, p. 508 (1990)]. However, these methods involve the following disad-vantages.

1) A plant in which a coat protein gene of a certain virus is expressed shows resistance to the infection of the parent virus but does not show resistance to viruses of other species at all. The resistance to a virus obtained by the expression of its coat protein gene is specific to the concerned virus. The coat protein of a virus differs with that of different virus, so that, in order to give resistance to plural viruses, it is required to transduce all the coat protein genes of the plural viruses into a plant. Actually, there is a report that coat protein genes of both a potato virus X and a potato virus Y were integrated into a potato and expressed therein to produce a plant having resistance to the two viruses [*Bio/technology*, vol. 8, p. 750 (1990)]. However,it is obvious that such a method as above is not realistic because it requires a great deal of labor to produce a plant having resistance simultaneously to 4 or more species of viruses.

In the case, also, of a method for making a satellite RNA express, the resistance to a virus to be obtained is specific to the concerned virus. In addition, this method is lack of general application because it is inapplicable if a pathogenic virus carries no satellite RNA.

2) The method for making a coat protein gene express is utilizable only after a pathogenic virus is isolated, the genetic structure of the virus is elucidated and a coat protein gene of the virus is identified. Thus, it is inapplicable to unknown viruses.

3) A viral gene generally has high probability of causing mutation. For example, to a virus-resistant variety produced by the conventional techniques such as cross-breeding and the like, the development of a viral strain overcoming this resistance (an overcomer) is often observed in the natural world. Also to a virus-resistant plant obtained according to genetic recombination technology, there is a possibility of appearance of such an overcomer.

DISCLOSURE OF THE INVENTION

The present invention purposes to produce a plant resistant against plural RNA viruses by integrating a single gene into a chromosome of a plant and making the gene express.

RNA in a cell is generally single-stranded and retains various important functions like messenger RNA, transfer RNA, etc. Contrary to this, double-strand RNA does not exist in a cell usually. However, a gene of a certain virus is double-strand RNA, and a virus whose gene is single-strand RNA goes through the double-strand state in the process of replication in the cell [Dictionary of Biochemistry, the 2nd edition, p. 961, Tokyo Kagaku-dojin (1990)]. That is, when a cell is infected with a RNA virus, there appears a double-strand RNA, which is a viral replication intermediate.

Then, the present inventors paid attention to that most of plant viruses are RNA viruses and studied intensively with an expectation that, when an enzyme, which does not break down single-strand RNA but specifically breaks down double-strand RNA alone, is expressed in a plant, the plant would show resistance to most of RNA viruses. As a result of it, they completed the present invention. As far as the present inventors know, such an attempt has not been made at all so far.

That is, the gist of the present invention lies in providing a method for producing plants resistant against RNA viruses by integrating a DNA sequence, which encodes a protein having an enzyme activity specifically breaking down a double-strand RNA, into a chromosome of a plant and making the DNA sequence express in the plant cells, and a plant resistant against RNA viruses obtained according to such a method as above.

Hereinafter, the present invention will be described in detail.

1) DNA Sequence Encoding Protein Having Enzyme Activity Specifically Breaking down Double-strand RNA The protein having an enzyme activity specifically breaking down double-strand RNA (hereinafter, referred to as "the double-strand RNase") means a protein having a ribonuclease (hereinafter, referred to as "RNase" occasionally) which breaks down double-strand RNA but hardly does single-strand RNA. As the double-strand RNase, RNase derived from *Escherichia coli*, a ribonuclease encoded in pacI gene derived from yeast, etc. are known.

In the present invention, any of these various double-strand RNases existing in the natural world may be used also. In addition, modified double-strand RNases prepared by subjecting the above double-strand RNases to substitution, deletion, addition and insertion of various amino acids may be used for the present invention as far as they retain activities of specifically digesting the double-strand RNA. In the present invention, the wording "substantially" in the case using as "substantially (existing double-strand RNase)" means that not only naturally existing double-strand RNases but also these modified double-strand RNases are included.

In the examples to be described later, although the pacI gene derived from yeast *Schizosaccharomyces pombe* is used as a DNA sequence encoding double-strand RNase, it goes without saying that the DNA sequence encoding double-strand RNase which can be used for attaining the purpose of the present invention, is nowise restricted to this pacI gene.

In addition, in case, generally, that a certain DNA sequence encodes a polypeptide carrying a certain amino acid sequence, plural DNA sequences corresponding to one amino acid sequence exist because there exist plural genetic codes (codons) corresponding to one amino acid sequence (degenerate isomers). In the case, also, of a DNA sequence encoding a double-strand RNase to be used in the present invention, it goes without saying that an arbitrary genetic code can be used as far as it does not change the amino acid sequence of a polypeptide which it encodes.

Because the whole base sequence of the pacI gene has been known already [*EMBO J.*, vol. 10, p.221 (1991)], it seems obvious for those skilled in the art that this gene can be obtained by isolating the same from yeast *Schizosaccharomyces pombe* (e.g., ATCC 2478 strain, etc.) or by chemically synthesizing a part or the whole of it based on this known base sequence. In addition to the pacI gene, the whole base sequence of a gene of the RNase as double-strand RNase derived from *Escherichia coli* has been known [*Nucleic Acids Res.*, vol. 13, p. 4677 (1985)].

2) Expression of DNA Sequence Encoding Double-strand RNase

In order that a DNA sequence encoding a double-strand RNase is expressed in a genetically recombined plant, it is required that at least this DNA sequence is transcribed into RNA. In case of integrating a foreign gene into a chromosome of a plant cell, it is possible to integrate a DNA sequence encoding a double-strand RNase independently and to make the RNase express because it has been known that the foreign gene is integrated down stream of a promoter on the chromosome in a certain probability [*EMBO J.*, vol. 6, p. 3891 (1987)]. However, it is preferred that the DNA sequence is integrated after previously ligating a suitable promoter and a suitable terminator sequence thereto.

In this case, as the promoter, all the promoters which have been known to function in a plant cell, specifically, a promoter of a gene encoding a small subunit of ribulose-1, 5-biphosphate carboxylase, a promoter of a nopaline synthesizingenzyme gene, a promoter producing 19S-RNA of a cauliflower mosaic virus, a promoter producing 35S-RNA of a cauliflower mosaic virus (CaMV 35S promoter) [*Proc. Natl. Acad. Sci. USA*, vol. 83, p. 2358; *Plant Cell Rep.*, vol. 4, p. 355 (1985); *Cell*, vol. 30, p. 763 (1982); and *Nature*, vol. 313, p. 810 (1985)], etc. can be used. Also as the terminator, all the terminators which has been known to function in a plant cell can be used. Specifically, a terminator of a nopaline-synthesizing enzyme gene, a terminator of an octopine-synthesizing-enzyme gene [*J. Mol. Appl. Gen.*, vol. 1, p. 561 (1982) and *EMBO J.*, vol. 3, p. 835 (1984)], etc. can be used.

3) Integration of DNA Sequence Encoding Double-strand RNase into Plant

In order to transduce a DNA sequence encoding double-strand RNase into a plant cell, various methods which have been already reported and established, for example, a method using the Ti plasmid of *Agrobacterium tumfaciens* as a vector, vector, a method for directly transducing DNA into a plant section or a plant protoplast, etc. can be used suitably according to the aimed plant species (see, for example, Genetic Transformation and Gene Expression of Plants; A Laboratory Manual", Draper, J. et al eds., Blackwell Scientific Publications, 1988). Generally, in case that a plant into which a gene is transduced is a dicotyledon, there are many cases where it is preferable to use the Ti plasmid vector. In case of a monocotyledon and a dicotyledon which is difficult to be infected with an agrobacterium, physical transduction methods such as electroporation and the like are preferable. As plant materials to be used for gene transduction, anything suitable can be selected from a leaf section, a stem section, a tuber section, a protoplast, a callus, pollen, etc. depending upon a transduction method. The transformed plant tissue or cell is cultured under suitable conditions according to a plant species, and whereby a transformed plant can be reproduced.

BRIEF DESCRIPTION OF THE DRAWINGS

FIG. 4 is a photograph showing the results of electrophoresis for detecting TMV coat protein in leaves of a tobacco (Samsun) inoculated with a tobacco mosaic virus (TMV). On the 11th day after inoculation of the TMV, the whole protein were extracted from the virus-inoculated upper leaves of non-transformants (controls), the β-GUS transgenic tobacco (β GUS) and pacI #1, #2 and #4 transgenic tobacco (Samsun) (the lane for TMV +), which are all on the 11th day after inoculation of TMV, or the upper leaves of a tobacco into which the TMV is not inoculated (the lane for TMV –), and the extracts were respectively reacted with anti-TMV rabbit sera.

The degree of disease symptom was shown two-stagewise as follows.

| | |
|---|---|
| After the inoculation of TMV, disease symptoms slightly appeared on the upper leaves | + |
| Disease symptoms became prominent | ++ |

Figure 7:
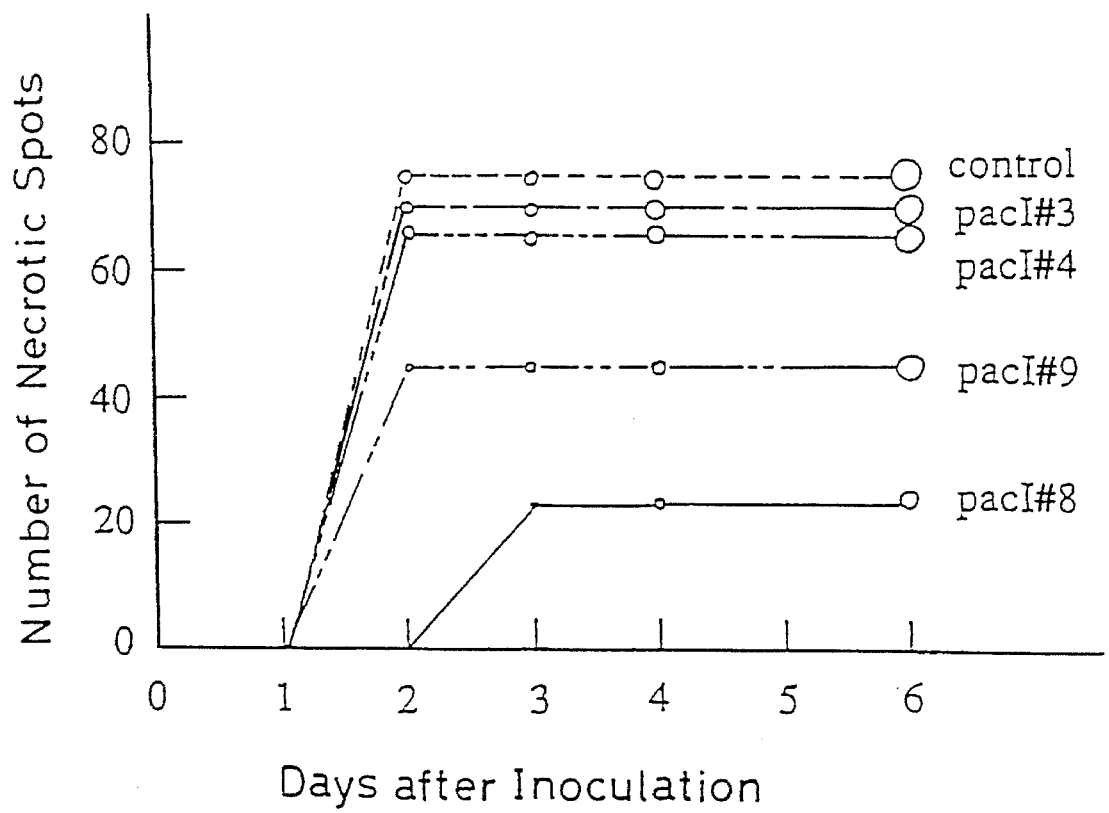

FIG. 7 is a graph showing changes in the number and the size of necrotic spot appeared on the TMV-inoculated leaves of a non-transformant (control) and pacI #3, #4, #8 and #9 transformed tobaccos (Xanthi nc). The ordinate indicates the number of necrotic spots in the left half area of the inoculated leaves and the abscissa indicates the time after infection. The relative size of a necrotic spot is indicated by the size of ○.

Figure 8A:
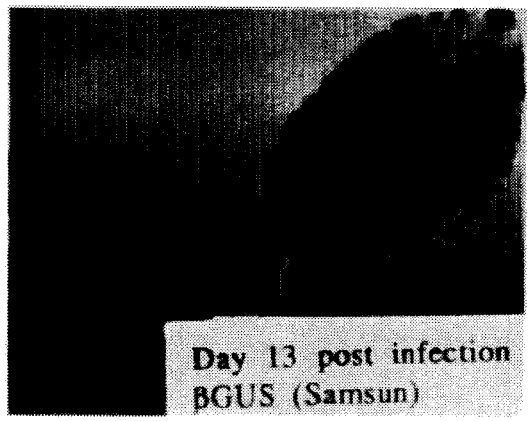
Figure 8B:
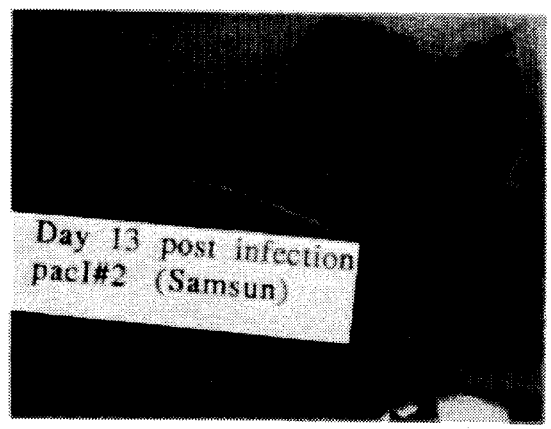
Figure 8C:
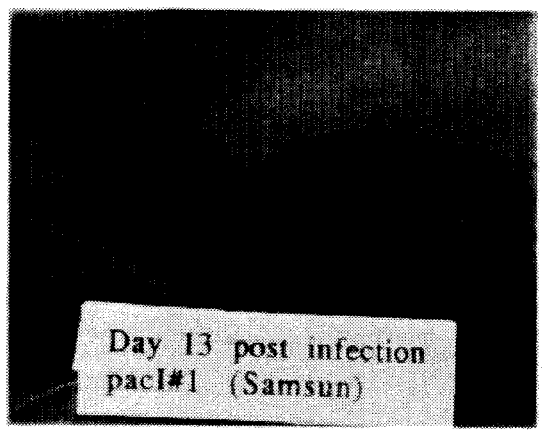

FIG. 8 is photographs of plants giving disease symptoms found in a β-GUS transgenic tobacco (β GUS) and pacI #1 and #2 transgenic tobaccos (Samsun) on the 13th day after inoculation of CMV.

Figure 9:
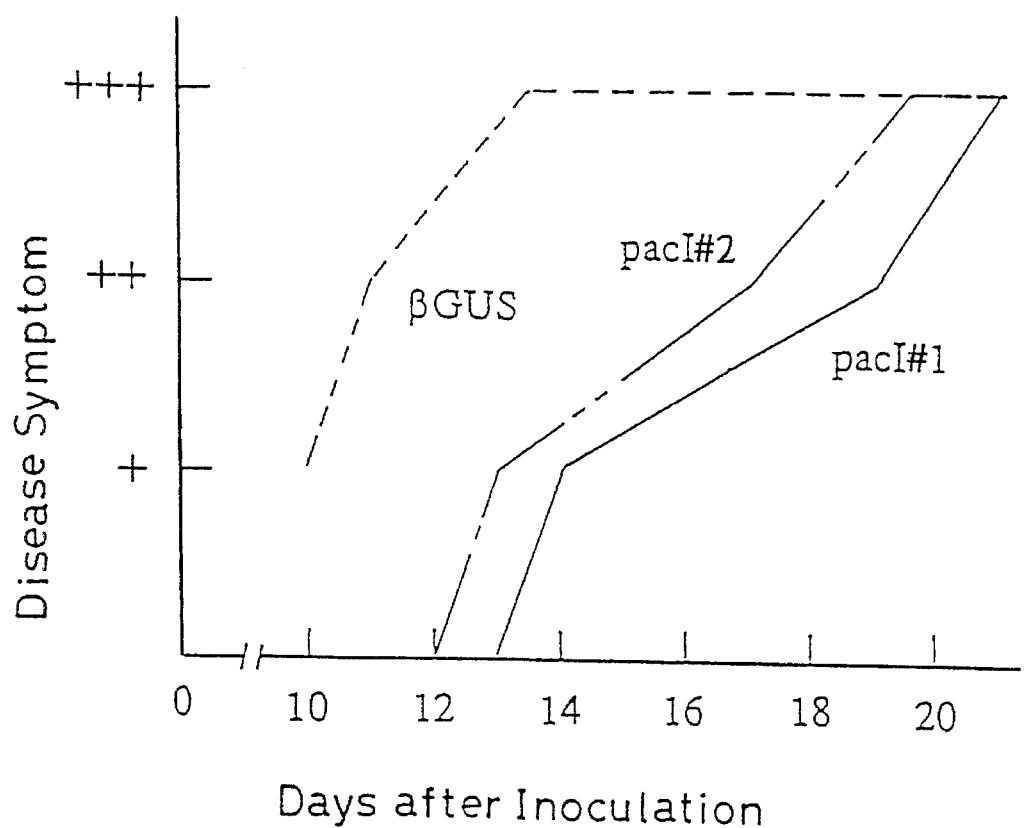

FIG. 9 is a graph showing the process of the appearance of disease symptoms in a β-GUS transgenic tobacco (β GUS) and pacI #1 and #2 transgenic tobaccos (Samsun) after the inoculation of CMV. The degree of disease symptom was shown three-stagewise as follows.

| | |
|---|---|
| Appearance of slightly yellowed site on part of a leaf | + |
| Intermediate state between + and +++ | ++ |
| Appearance of the state where yellowing spread on the whole leaf | +++ |

Figure 10:
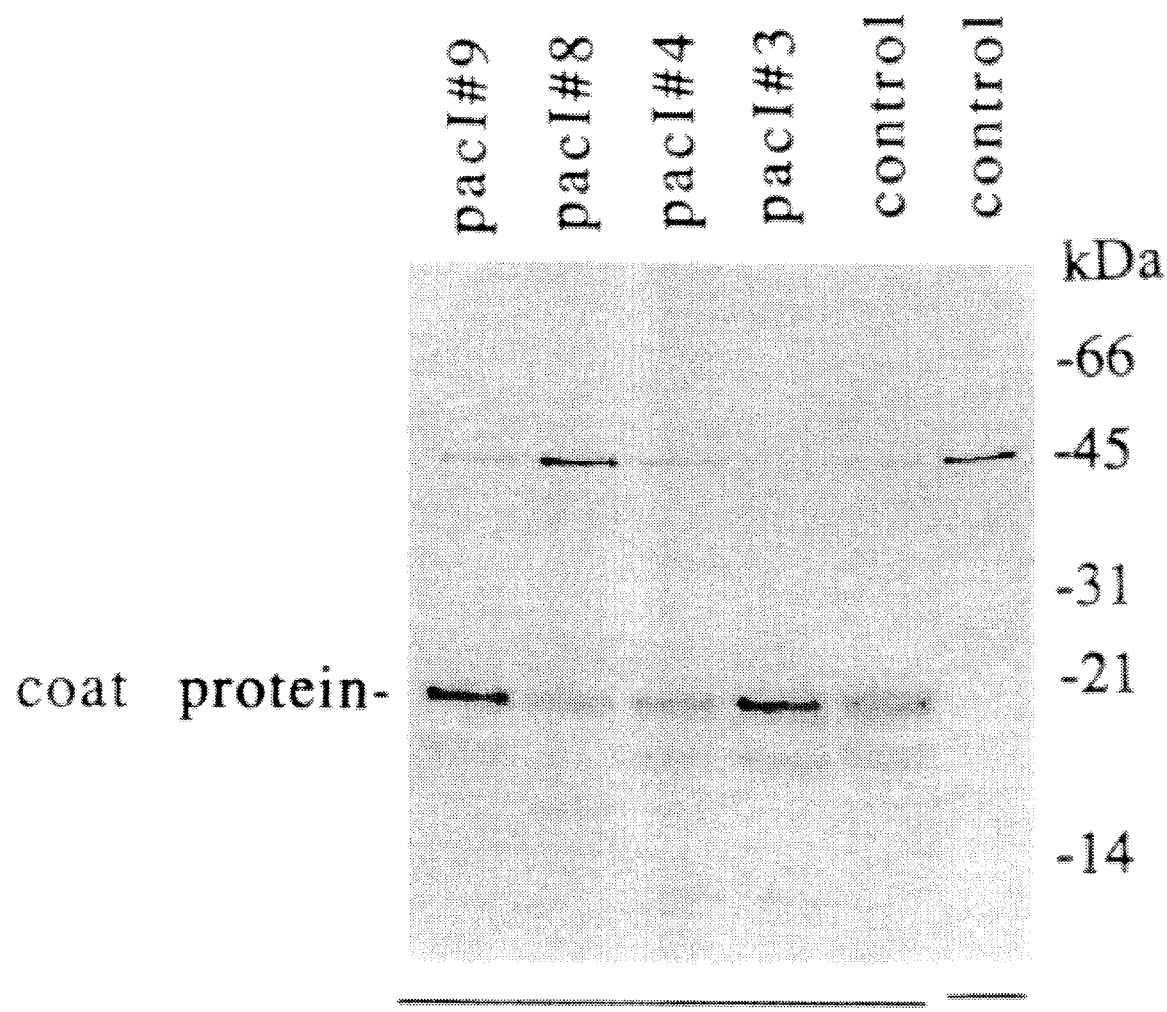
Figure 11A:
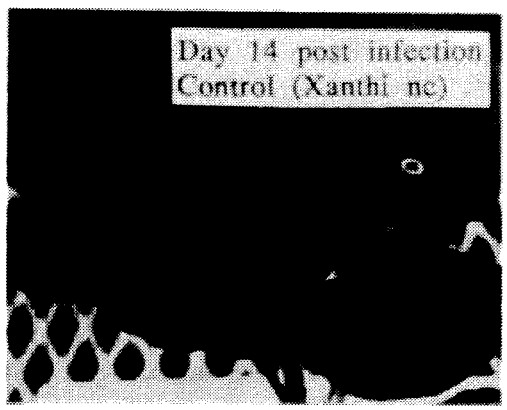
Figure 11B:
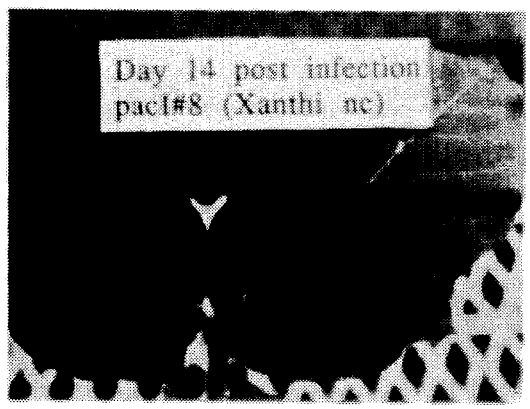
Figure 11C:
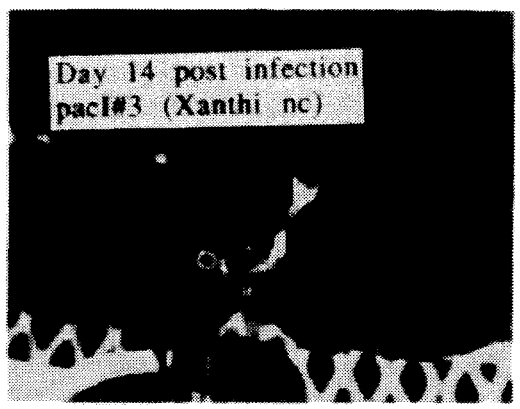
Figure 11D:
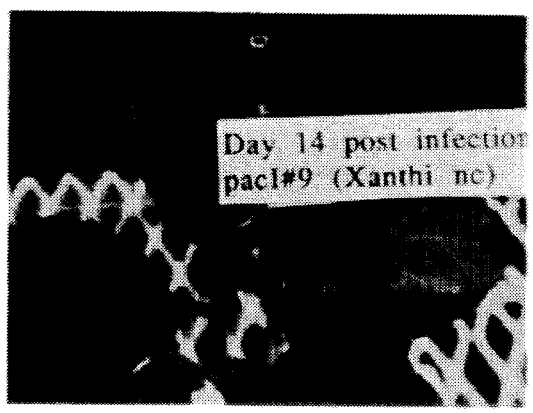
Figure 11E:
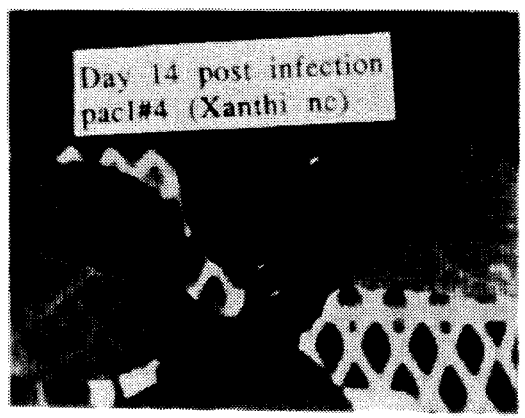

FIG. 10 is a photograph showing the result of electrophoresis for detecting the CMV coat protein in leaves of CMV-inoculated tobacco (Xanthi nc). The whole protein was extracted from the virus-inoculated upper leaves of nontransformant (controls) and pacI #3, #4, #8 and #9 transformed tobaccos (Xanthi nc) (the lane for CMV +), all of which are on the 14th day after inoculation of CMV, or the upper leaves of a tobacco into which the CMV is not inoculated (the lane for CMV–), and the extracts were respectively reacted with anti-CMV rabbit sera.

FIG. 11 is photographs of plants giving disease symptoms found in a non-transformant (control) and pacI #3, #4, #8 and #9 transformed tobacco (Xanthi nc) on the 14th day after inoculation of CMV.

Figure 12:
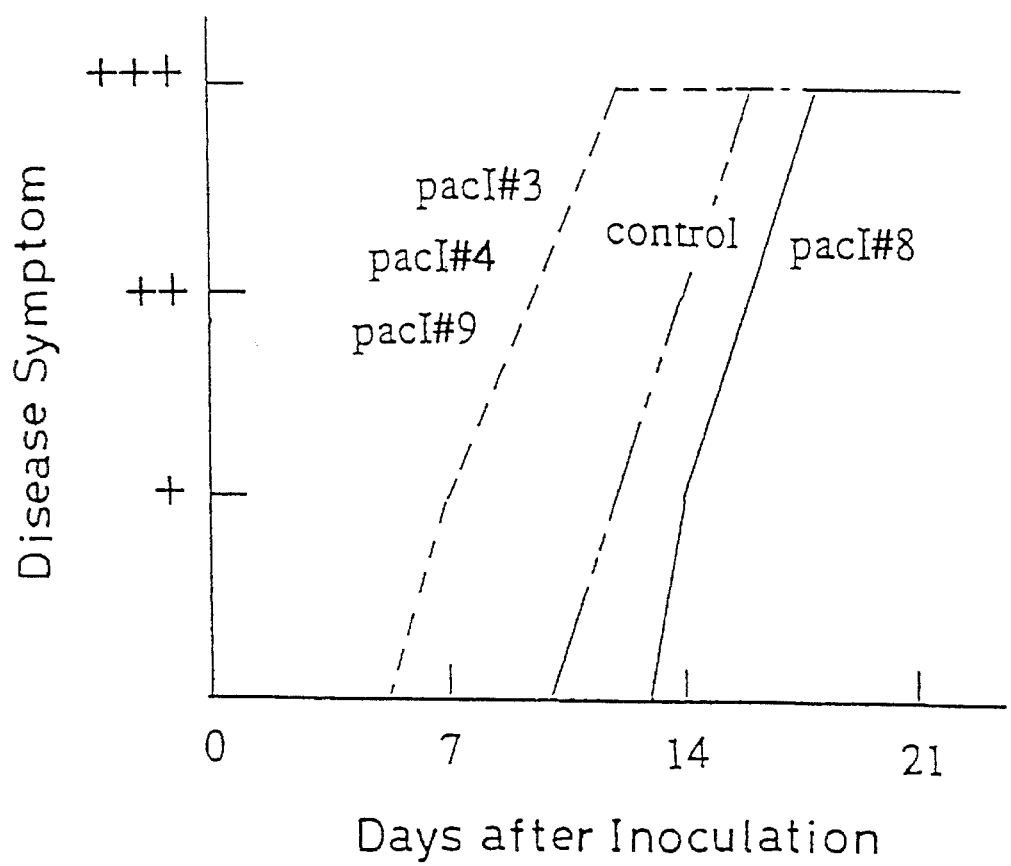

FIG. 12 is a graph showing the process of the appearance of disease symptoms in a non-transformant (control) and pacI #3, #4, #8 and #2 transformed tobaccos (Xanthi nc) after the inoculation of CMV. The degree of disease symptoms was shown three-stagewise as follows.

| | |
|---|---|
| Appearance of slightly yellowed site on part of a leaf | + |
| Intermediate state between + and +++ | ++ |
| Appearance of the state where yellowing spread on the whole leaf | +++ |

FIG. 13 is a graph showing the onset of disease after PVY inoculation in a non-transformant (control) and pacI #3, #4 and #8 transformed tobaccos (Xanthi nc). The PVY was inoculated into 6 individuals each of tobacco clones, and the number of diseased individual was given in the graph. FIG. 14 (SEQ ID NO:1) is a chart showing a design of RNase III gene modified for plant expression. The translational region of amino acids is written in capital letters, while the non-translational part is written in small letters. Nicks of each synthetic oligo DNA are indicated with underlines. And, the PCR primer part is indicated with a net pattern.

Figure 15:
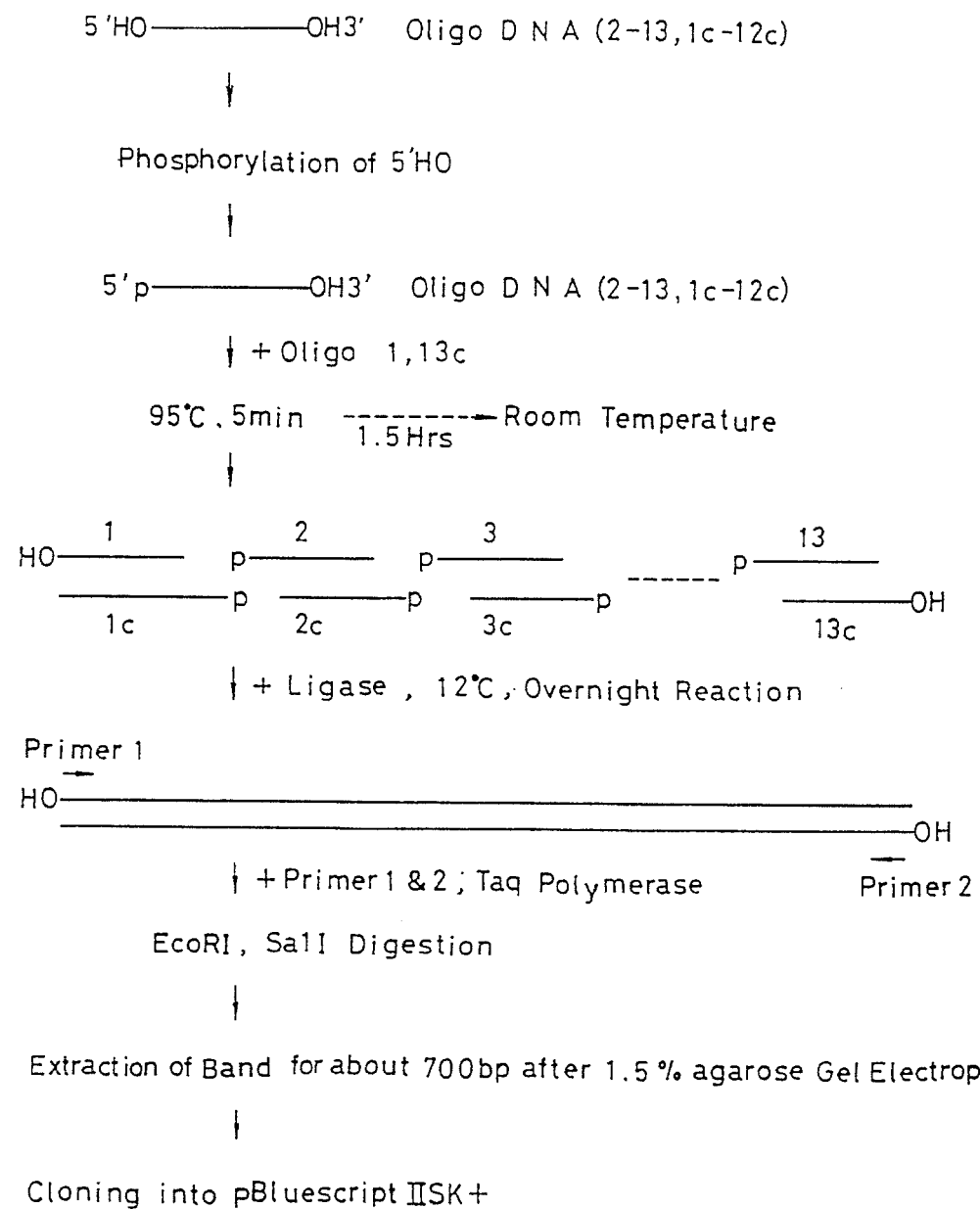

FIG. 15 is a schematic view showing a method for amplifying the synthesized DNA by ligase reaction and PCR.

FIG. 16 is photographs of plants showing TMV-inoculated leaves of R1 plants (pacI #8-2, pacI #8-4 and pacI #8-3) and a control on the 3rd day after inoculation of TMV.

THE BEST EMBODIMENT OF THE INVENTION

Hereinafter, the present invention is described more specifically, referring to examples. However, the scope of the present invention is nowise restricted to the examples set forth below.

In the following examples, the aforementioned pacI gene was used as a DNA sequence for a double-strand RNase and CaMV 35S promoter is used as a promoter to make this gene express in a plant. The *E. coli*-derived β-glucuronidase gene (β GUS) on the pBI121 vector [*EMBO J.*, vol. 6, p. 3901 (1987)] was replaced with a DNA containing a region encoding double-strand RNase protein of the pacI gene, thereby constructing a plasmid for expressing the pacI gene in a plant.

Tobaccos (strains Samsun and Xanthi nc) were used as host plants for confirming the effect of the present invention, and transformants of the tobaccos were obtained according to the leaf disc technique [Science, vol. 223, p. 496 (1985)] using agrobacterium into which the pBI121 plasmid containing the pacI genes had been transduced.

The expression of a pacI gene product in the transformed plants was immunochemically detected by using anti-pacI antibodies after electrophoresing the crude extracts of leaves on SDS poly-acrylamidegel. As a result of viral infection test using a tobacco mosaic virus (TMV-OM strain), a cucumber mosaic virus (CMV-Y strain) and a potato virus Y (PVY-T strain), transformed tobacco plants expressing pacI genes highly showed resistance to all the viruses.

EXAMPLE 1

Figure 1:
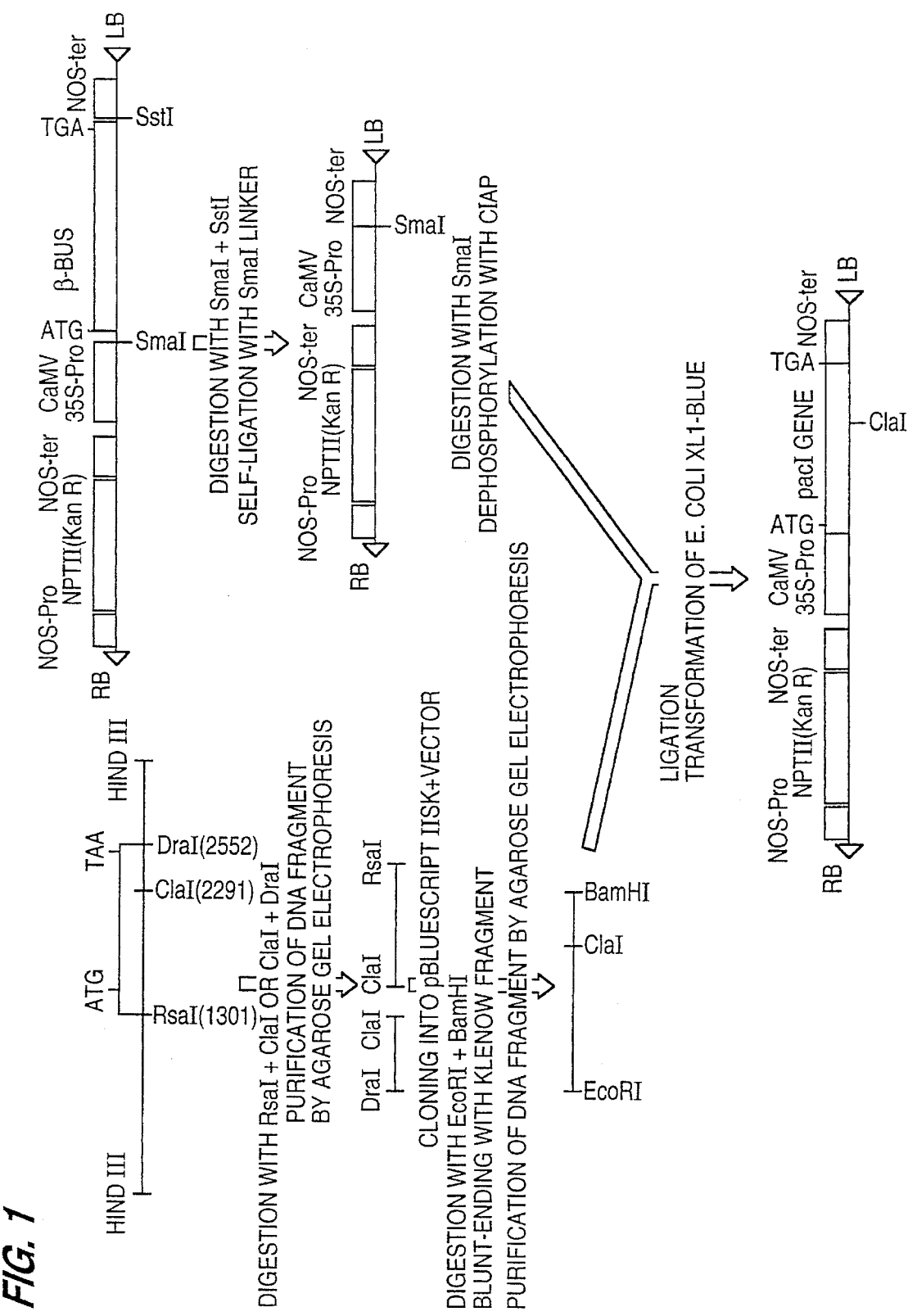
FIG. 1 is a chart showing the construction of a plant transforming vector containing the pacI gene.

Construction of plasmid to be used for producing transformed plant (FIG. 1)

About 3-kbp Hind fragments containing pacI genes derived from *Schizosaccharomyces pombe* [*EMBO J.*, vol. 10, p. 221 (1991)] were digested with ClaI+RasI and ClaI+DraI, the digested fragments were respectively fractionated by 1% agarose gel electro-phoresis, and then about 900-bp RasI-ClaI fragment and about 250-bp ClaI-DraI fragment were extracted from agarose gel and purified. These two fragments were subcloned into the SmaI site of a pBluescript IISK+ (manufactured by Stratagene) vector, thereby obtaining a plasmid where about 1,150-bp pacI gene was inserted. This plasmid was purified, digested with EcoRI+BamHI, blunt-ended by the Klenow fragment of DNA polymerase I (manufactured by Takara Shuzo Co., Ltd.) and then electrophoresed on agarose gel to purify a blunt-ended DNA fragment containing about 1,150 bp pacI gene. On the other hand, pBI121 vector plasmid (manufactured by Clonetech) was digested with SmaI+SstI, freed from the β-GUS gene and then self-ligated through a SmaI linker to make pBI121-GUS. A fragment prepared by digesting this pBI121-GUS vector plasmid with SmaI and subsequently treating with alkaline phosphatase (CIAP; manufactured by Boehringer). The DNA fragment containing about 1,150-bp pacI gene obtained above were ligated with the pBI121-GUS digested with SmaI and then transformed an *E. coli* XL1-Blue strain (manufactured by Stratagene). A plasmid in which the pacI gene was inserted on the downstream of the CaMV 35S promoter in the right direction is called pBI121+pacI.

EXAMPLE 2

Transformation of tobaccos with Agrobacterium

For the transformation, the Samsun strain and the Xanthi nc strain of *Nicotiana tabacum* were used. By conjugative transmission using *E. coli* C600 strain carrying the pRK2013 plasmid as a helper, the plasmid pBI121+pacI was transmitted from the *E. coli* XL1-Blue strain to *Agrobacterium tumefaciens* LBA4404 strain [see, e.g., DNA Cloning, D. M. Glover, IRL Press (1985)].

After infecting leaf sections of the tobaccos with the *Agrobacterium tumefaciens*, the leaf sections were placed on MS-B5 media [a medium prepared by adding vitamin B5 to the Murashige & Skoog's basal medium <*Physiol. Plant.*, vol. 15, p. 473 (1962)>], from which transformed tissues were selected. When shoots came out, they were moved into hormone-free MS media and rooted there. The obtained transformed plants were subcultured by sterile in vitro culture.

Example 3 Detection of pacI gene product in the transformed tobaccos

Leaves of the transformed tobaccos cultured in vitro were placed in equal quantities of an extraction buffer A [containing 50 mM Tris-HCl pH 7.5, 0.25M KCl, 2 mM EDTA, 1 mM mercaptoethanol, 0.1 mM dithiothreitol (DTT), 200 µM phenyl-methylsulfonyl fluoride (PMSF), 20 µg/ml leupeptin, 50 µg/ml bovine lung approtinine and 0.05% sodium deoxycholate) and homogenized using a Teflon pestle homogenizer (20 ml). After centrifuging the homogenized mixture at 15,000 rpm at 4° C. for 20 minutes, the supernatant was taken out. After measuring the quantity of protein according to the Bradley's method (the protein assay kit of Bio-Rad Laboratories), 150 µg/sample of protein was taken out and electrophoresed on SDS-polyacrylamide gel (10% acrylamide). After the electro-phoresis, the protein was transcribed on a polyvinylidenedifluoride (PVDF) membrane (manufactured by Millipore) using a semidry blotting apparatus (manufactured by Saltrius).

*E. coli* S4 gene was used to produce the fused protein between the pacI gene product and *E. coli* S4 protein, the obtained fused protein was purified, and a rabbit was immunized with this to obtain an antiserum to the pacI gene products. An immunoglobulin G fraction of this antiserum was obtained, and then a fraction passing through a cellulose column to which S4 protein had been bound was obtained. Subsequently, this fraction was adsorbed on an affinity column to which the pacI gene product produced by *E. coli* [*EMBO J.*, vol. 10, p. 221 (1991)] had been bound. After washing, the column on which the fraction had been adsorbed was eluted to obtain an anti-pacI antibody solution.

The proteins of the leaves of the transformed tobaccos transfered on the PVDF membrane were reacted with the above anti-pacI antibody, and proteins reactive to the antibody were detected using a peroxidase ABC kit (Vectastain; manufactured by Funakoshi K.K.). In order to confirm that the proteins detected in this experiment are pacI gene products, the same experiment was carried out using an anti-pacI antibody which had been previously reacted with β-galactosidase-pacI fused protein produced by *E. coli*, the results of which were compared with the above experimental results.

Figure 2:
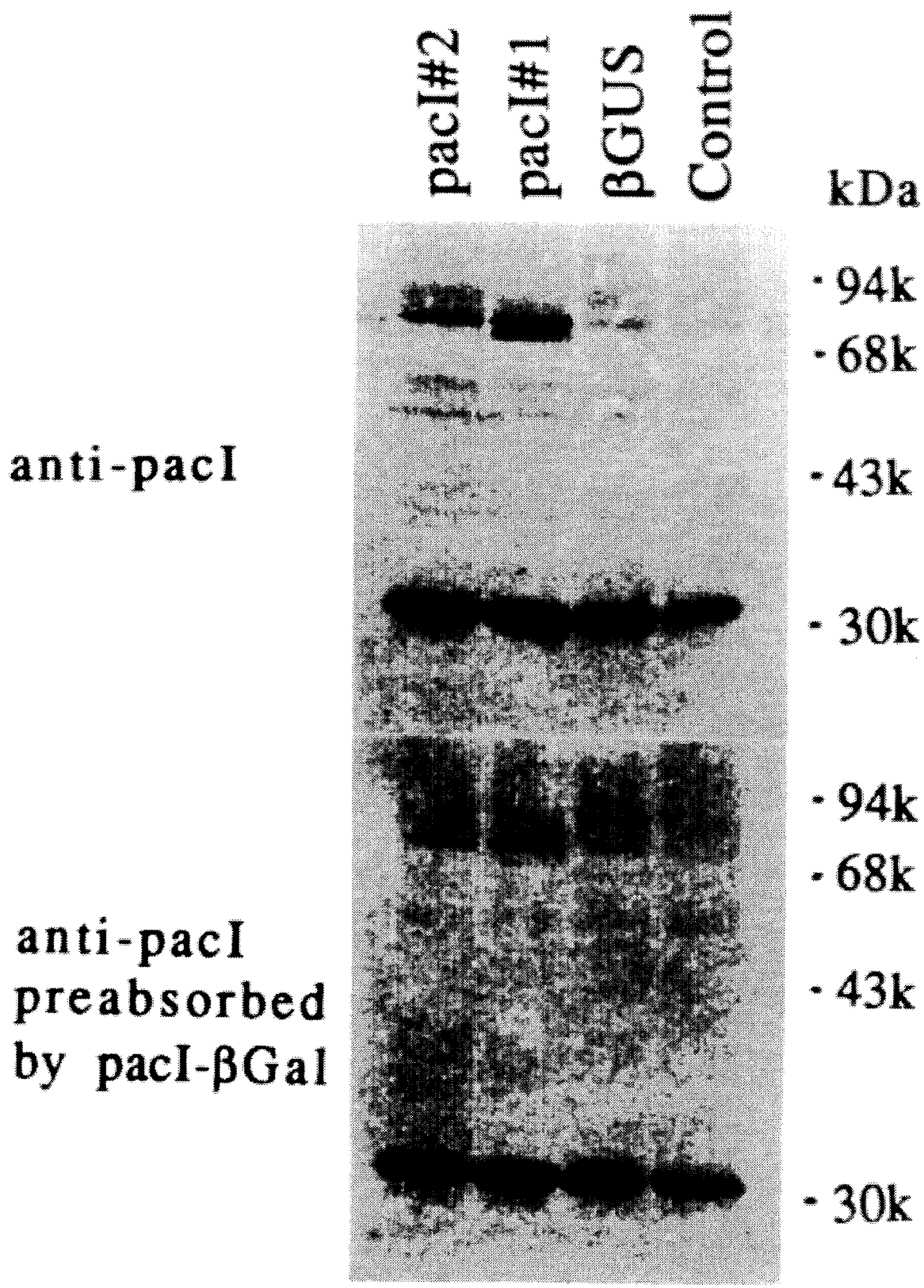
FIG. 2 is a photograph showing the results of electrophoresis for detecting the pacI gene product in leaves of the transformed tobacco (Samsun). Crude extracts of leaves of a non-transformant (control), the β-GUS transgenic tobacco (β GUS) and pacI #1 and #2 transformed tobaccos were reacted with anti-pacI antibodies (the lower panel) absorbed by anti-pacI antibody (the upper panel)-β-galactose-pacI fused protein.

In the case of the transformed tobacco (Samsun), a band (about 70 kDa) specifically reacting to the anti-pacI antibody, which were considered to be a pacI gene product, was detected from pacI #1 and #4 clones. On the other hand, in the case of the non-transformed tobacco and the pBI121 plasmid-transduced tobacco (which will be hereinafter referred to as "β-GUS transgenic tobacco") as controls and pacI #2 clone of the transformant, a band specifically reacting to the anti-pacI antibody was not detected (see FIG. 2; however, no result is shown with respect to the pacI #4 clone). Incidentally, as a result of examining the presence of mRNA of pacI genes in the plant cells of the transformants pacI #1 and #2, expression was recognized in both cases (no datum was shown). The reason why pacI protein is not detected in #2 clone is unclear.

Figure 3:
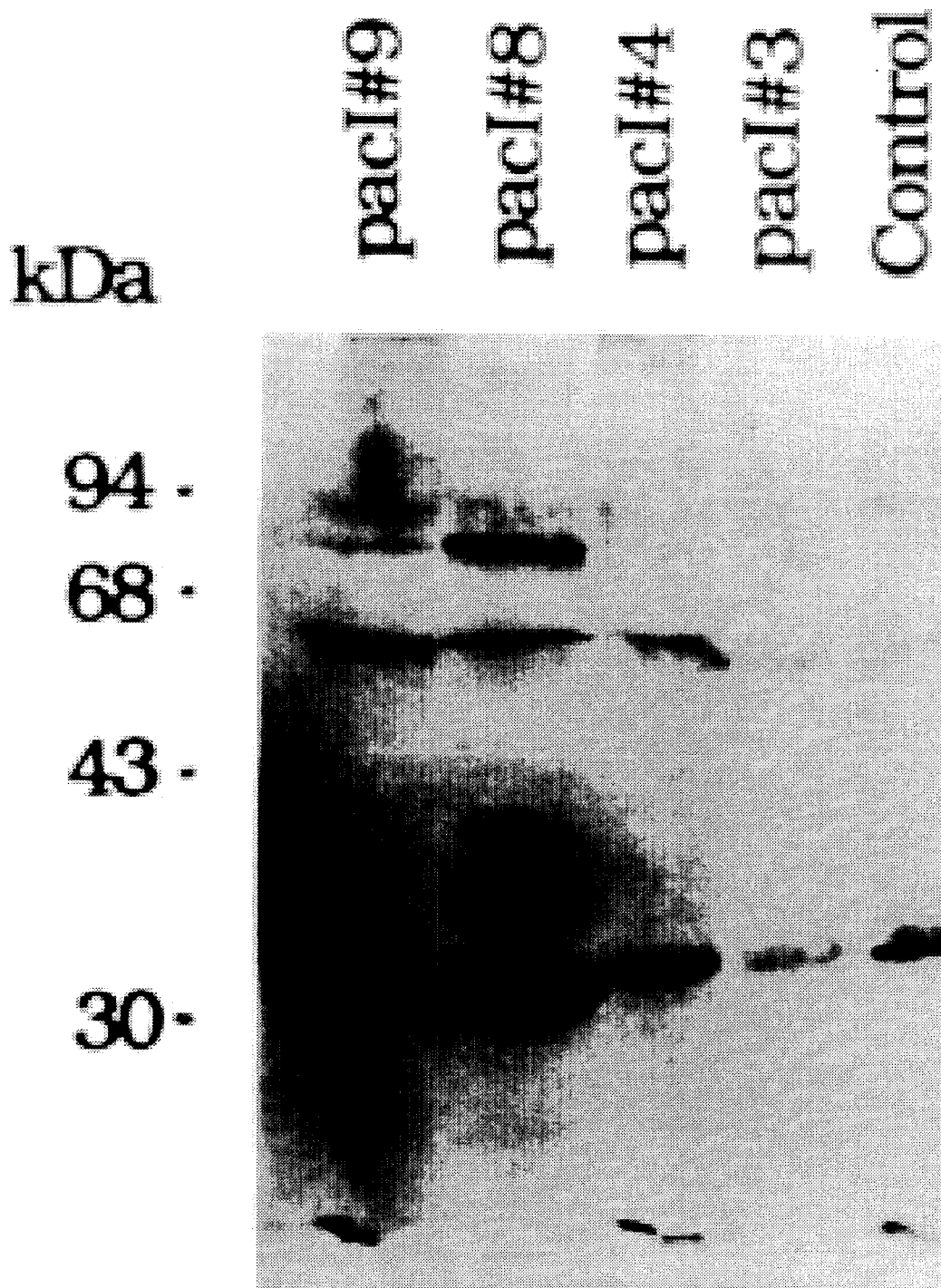
FIG. 3 is a photograph showing the results of electrophoresis for detecting the pacI gene product in leaves of the transformed tobacco (Xanthi nc). Crude extracts of leaves of a non-transformant (control) and pacI #3, #4, #8 and #9 transformed tobaccos (Xanthi nc) were reacted with anti-pacI antibodies.
Figure 5A:
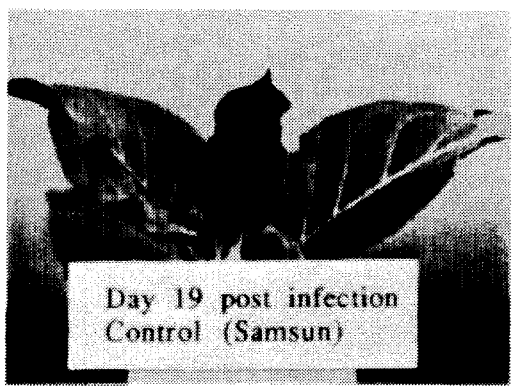
FIG. 5 is photographs of plants showing the appearance of disease symptoms in a non-transformant (control), the β-GUS transgenic tobacco (β-GUS) and pacI #1, #2 and #4 transgenic tobaccos (Samsun) on the 19th day after inoculation of TMV.
Figure 5B:
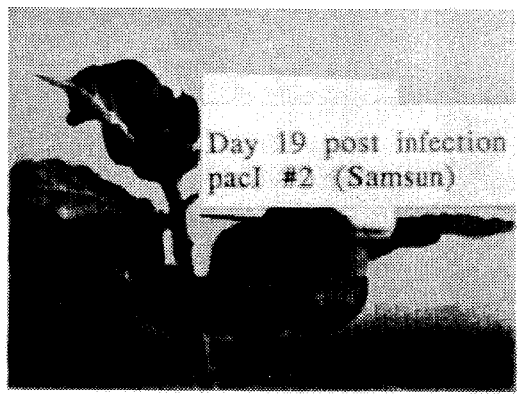
Figure 5C:
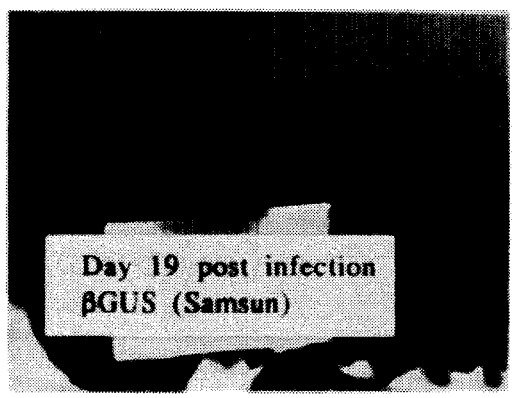
Figure 5D:
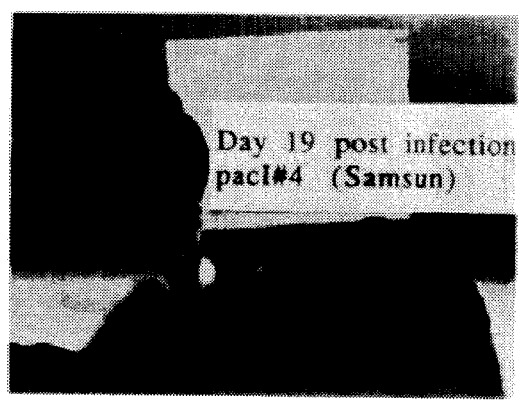
Figure 5E:
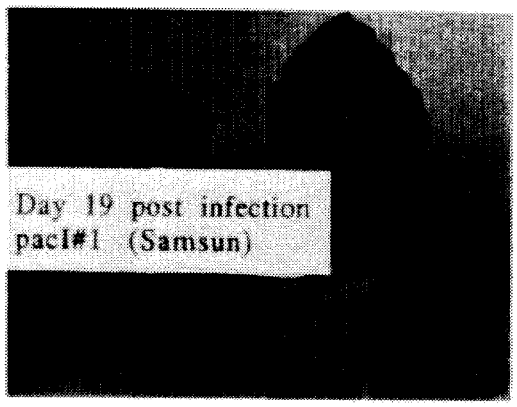

On the other hand, in the case of the transformed tobacco, a protein band (about 70 kDa) considered to be a pacI gene product was detected in pacI #8 clone. However, no pacI gene product was detected in the non-transformed tobacco as a control and in the clones of the transformant pacI #3, #4 and #9 (FIG. 3).

EXAMPLE 4

Detection of double-strand RNase activity of the pacI gene product

Leaves of a transgenic tobacco (Samsun) cultured in vitro were homogenized using an equal quantity of an extraction buffer B (an extraction buffer prepared by removing sodium deoxycholate from the extraction buffer A), the whole protein was extracted in the same manner as in Example 3. To the leaf extract equivalent to 200 µg of protein (diluted with the buffer B so as to make a volume of 43 µl), 1 µl of the anti-pacI antibody solution obtained in Example 3 or 1 µl of a phosphate buffer was added. The mixture solution was incubated at 4° C. for 2 hours. Subsequently, 5 µl of IgGsorb (Enzyme Center; manufactured by Funakoshi) was added to the incubate and centrifuged at 4° C. for 5 minutes. The supernatant was taken out, and the double-strand RNase activity in the supernatant was measured. The sample was reacted with tritium-labeled double-strand RNA substrates at 37° C. for 30 minutes in the following solution for reaction, and the radio-activity in a trichloroacetic acid (TCA)-insoluble fraction was measured [*EMBO J.*, vol. 10, p. 221 (1991)]. The value obtained by subtracting a value in the case of adding the anti-pacI antibody from a value in the case of not adding the antibody was decided as the double-strand RNase activity of the pacI gene product (Table 1).

[Reaction Mixture]

50 µl Sample
50 µl 2 × Reaction buffer (40 mM Tris-HCl pH 7.5, 0.2M KCl, 0.02M MgCl$_2$, 0.2 mM DTT, 50 µg/ml $^3$H polyA:polyU*)
*Preparation of the substrate $^3$H polyA:polyU

| | |
|---|---|
| 10 mg/ml polyA (Pharmacia) | 24.6 µl (246 µg) |
| 10 mg/ml polyU (Pharmacia) | 25 µl (250 µg) |
| 20 µCi/ml $^3$H polyA (Amersham) | 250 µl (About 4 µg) |
| 3M KCl | 330 µl |
| 1M Tris-HCl pH 7.5 | 20 µl |

The total volume was brought to 1 ml with sterile distilled water, and the reaction was carried out overnight at 25° C.

TABLE 1

Double-strand RNase Activity of pacI gene Product in Leaf Extract of pacI Transgenic Tobacco (Samsun)

| Tobacco | − Antibody | + Antibody | pacI Product Activity |
|---|---|---|---|
| Non-transformant | 1688 cpm | 1614 cpm | 74 cpm |
| β-GUS | 2106 | 2022 | 84 |
| pacI #1 | 1919 | 1605 | 314 |
| pacI #2 | 2127 | 2076 | 51 |

Only the transgenic tobacco pacI #1 in which leaf extract a band specifically reacting to the anti-pacI antibody had been detected in Example 3 showed a significant double-strand RNase activity of the pacI gene product.

EXAMPLE 5

Test of inoculation with tobacco mosaic virus (TMV)
1) pBI121+pacI plasmid-transformed tobacco (Samsun) The transformed plants after 3 week habituation were inoculated with the TMV-OM strain (0.1 μg/ml) suspended in a 10 mM sodium phosphate buffer (pH 7.4) on the surface of their leaves with a carborundum as an abrasive.

On the 11th day after inoculation, a leaf growing upper than that inoculated with the virus were partially cut off. From the leaves cut, the whole protein was extracted with a SDS buffer (2% SDS, 80 mM Tris-HCl pH 6.8, 2% 2-mercaptoethanol, 10% glycerin) five times the weight of the leaves. Each sample was diluted 100-fold with a sample buffer for SDS electro-phoresis (50 mM Tris-HCl pH 6.8, 1% SDS, 1% 2-mercaptoethanol, 10% glycerin, 0.05% bromophenol blue), and then 10 μl of the diluted sample was fractionated by SDS polyacrylamide electro-phoresis (12.5% acrylamide). The protein was transfered onto a PVDF membrane, from which the TMV in the leaves of the infected plant was detected using an anti-TMV serum (rabbit; diluted 300-fold) and a peroxidase ABC kit.

The TMV was detected in the virus-inoculated upper leaves of the transgenic tobacco (Samsun) pacI #2 and the controls (non-transformant and β-GUS transgenic tobacco) on the 11th day after inoculation, whereas nothing was detected from the transgenic tobacco #1. From #4, though the TMV was detected, the quantity of TMV coat protein was obviously smaller than #2 and the controls.

Figure 6:
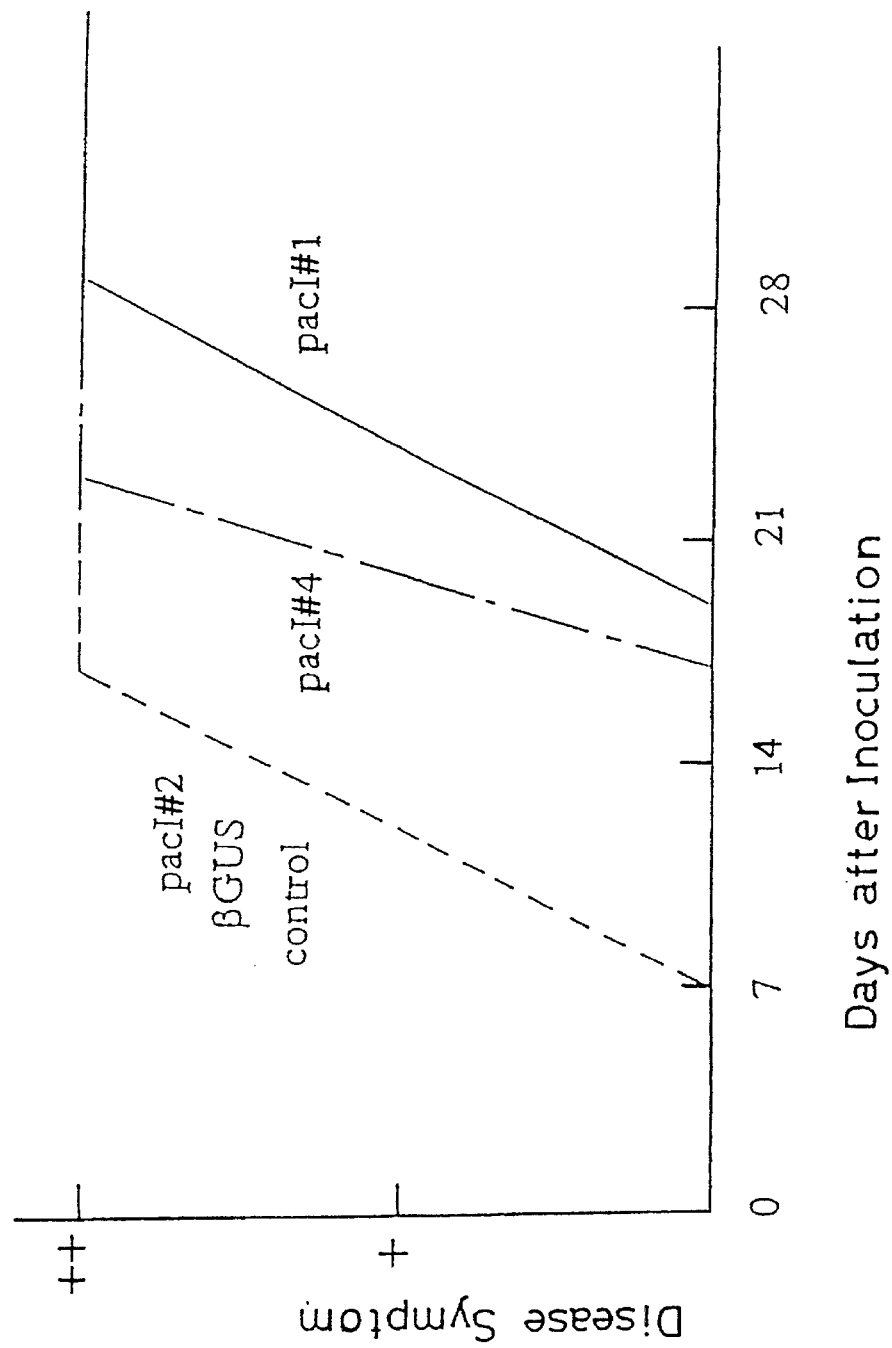
FIG. 6 is a graph showing the process of the appearance of disease symptoms in a non-transformant (control), a β-GUS transgenic tobacco (β GUS) and pacI #1, #2 and #4 transgenic tobaccos (Samsun) after the inoculation of TMV.

The development of mosaic disease symptoms (on the 19th day after inoculation) resulting from the viral infection in these transgenic tobaccos (Samsun) is shown in FIG. 5. In the transgenic tobacco pacI #1 in which a protein to be specifically reacted with the anti-pacI antibody was expressed and the double-strand RNase activity of the pacI gene product was detected (see Examples 3 and 4), the obvious delay in development of mosaic disease symptom was recognized. On the other hand, in the transgenic tobacco pacI #2 in which the expression of the pacI gene product had not been recognized, the delay in development of disease symptoms was not recognized also. In FIG. 6, the development of disease symptoms after the infection by the TMV was graphically shown.

2) pBI121+pacI plasmid-transformed tobacco (Xanthi nc)

In the same manner as in the case of Samsun, the TMV-OM (0.1 μg/ml) was inoculated into a plant after 3 week habituation. The 4th or 5th leaf from the bottom was inoculated with the virus. After infecting with the virus, the development of a necrotic local lesions in the inoculated leaves was observed, and the time of development, the number and the size of them were graphically shown (FIG. 7).

In the transformed tobacco (Xanthi nc) in which a protein to be specifically reacted with the anti-pacI antibody had been expressed (see Example 3), not only the development of necrotic local lesions was delayed but also the number and the size were decreased. On the other hand, the transformed tobaccos pacI #3, #4 and #9 in which the expression of the pacI gene protein had not been found, no distinct difference from the control (non-transformant) was recognized in the time of development, the number and the size of a necrotic local lesions.

The above results mean that the expression of the double-strand RNase (pacI gene product) in tobacco plants (Samsun and Xanthi nc) suppresses the replication of the TMV.

EXAMPLE 6

Test of inoculation with cucumber mosaic virus (CMV)
1) pBI121+pacI plasmid-transduced tobacco (Samsun)

The transformed plants after 2 week habituation were inoculated with the CMV-Y strain (1 μg/ml) suspended in a 10 mM sodium phosphate buffer (pH 7.4) on the surface of their leaves using a Carborundum as an abrasive, and the development of disease symptoms after the viral inoculation was observed. The state of the development of disease symptoms in each tobacco plant on the 13th day after inoculation was shown in FIG. 8. In addition, the development of disease symptoms and the degree of yellowing to be appeared on leaves are graphically shown in FIG. 9.

In comparison with the β-GUS transgenic tobacco (Samsun) as a control, the development of disease symptoms were delayed in the pacI transgenic tobacco, and its disease symptoms (the degree of leaf yellowing) on the 19th day after inoculation was in order of β-GUS>pacI #2>pacI #1.

2) pBI121+pacI plasmid-transduced tobacco (Xanthi nc)

In the same manner as in the case of Samsun, the CMV-Y (0.1 μg/ml) was inoculated into a plant after 2 week habituation. On the 14th day after the viral infection, a leaf (the third leaf from the top) growing upper than that inoculated with the virus was partially cut off. From the leaf cut, the whole protein was extracted in the same manner as in Example 5-1), fractionated and transfered onto a PVDF membrane, from which the CMV in the leaves of the infected plant was detected using an anti-CMV serum (rabbit; diluted about 2,000-fold) and a peroxidase ABC kit.

In the transformed tobacco (Xanthi nc) pacI #8, the decrease in the CMV coat protein in the upper leaf of the CMV-inoculated plant was recognized, as compared with the control and the transformed tobaccos pacI #3, #4 and #9 in which the expression of the pacI protein had not been observed (FIG. 10).

Disease symptoms (the degree of leaf yellowing) developed in the leaves of the control and the respective transformed plants on the 14th day after inoculation were shown in FIG. 11. In addition, the development of the disease symptoms and the degree of yellowing after virus inoculation were graphically shown in FIG. 12. As compared with the control and pacI #3, #4 and #9, the development of the disease symptoms were obviously delayed in the pacI transformed tobacco (Xanthi nc) pacI #8. These results mean that the replication of the CMV is suppressed in the transformed tobacco pacI #8.

EXAMPLE 7

Test of inoculation with potato virus Y (PVY)

Using the pBI121+pacI plasmid-transformed tobacco (Xanthi nc), a test of inoculation with a potato virus Y (PVY) was carried out.

After infection of *Nicotiana sylvestris* with the PVY necrosis line (PVY-T), 5-fold quantity of a 10 mM sodium phosphate buffer (pH 7.0, containing 20 mM 2-mercaptoethanol) was added to the infected leaves which had been dried and preserved, and this mixture was ground in a mortar. After the centrifugation, the supernatant was diluted 1,000-fold with the above buffer, and inoculated on the surface of the leaves of the transformed tobacco (Xanthi nc) after 2 week habituation.

After inoculation with the PVY-T into each 6 individuals of the control (non-transformant) and the transformed tobacco (Xanthi nc), disease symptoms were observed, and the number of individuals giving an obvious disease symptom (development of a necrotic spot) was shown in FIG. 13. In the transformed tobacco pacI #8 expressing the pacI protein, the appearance of a diseased individual was delayed in comparison with the control and the pacI transformed tobaccos #3 and #4 expressing no pacI protein, and, as same as in the case of the tests for the TMV and CMV inoculation, resistance to viruses owing to the pacI gene products expressed in the plants was also recognized with respect to the PVY.

EXAMPLE 8

Synthesis of modified RNase III gene for plant expression

In designing a modified RNase III gene for plant expression (FIG. 14), codons corresponding to amino acids were changed into those which are highly frequently used in plant genes [*Nucleic Acids Res.*, vol. 17, p. 477 (1989)] and the part in which adenine and thymine continued was replaced by guanine and cytosine so far as the amino acid sequence was not changed, based on the DNA sequence of the *E. coli*-RNase III gene [*Nucleic Acids Res.*, vol. 13, p. 4677 (1985); Corrigenda, 6400]. In addition, a restriction enzyme EcoRI-recognizing sequence was added before the translation initiation codon ( ATG ) on the 5'-end, and a restriction enzyme SalI-recognizing sequence was added behind the translation termination codon ( taa ) (bases written in small letters in FIG. 14). In addition, as indicated by dividing lines in FIG. 14, the synthesis of bases was carried out by dividing into 26 parts (1~13 and 1c~13c in FIG. 15). In the synthesis, a DNA synthesizer (A394) (manufactured by Applied Biosystems) was used.

The synthesized DNAs were purified using an OPC cartridge (manufactured by Applied Biosystems), and the DNA concentrations thereof were determined by measuring the absorbance at 260 nm by a spectrophotometer. The amplification of the ligated DNA was carried out by the PCR after simultaneously ligating all the synthesized DNAs [*Proc. Natl. Acad. Sci. USA*, vol. 88, p. 4084 (1991)]. As shown in FIG. 15, 25 pmol each of 24 synthesized DNAs, excluding the + strand synthetic DNA on the 5'-end (FIG. 15-1) and the − strand synthetic DNA on the 3'-end (FIG. 15-13c), were individually phosphorylated with T4 polynucleotide kinase in 15 µl each of a reaction mixture. After the completion of reaction, the DNA solutions were heated at 68° C. for 10 minutes. The 24 kinds of phosphorylated DNA solutions were collected into one tube. After adding 2.5 µl (10 pmol/µl) of unphosphorylated + strand synthetic DNA on the 5'-end and -strand on the 3'-end to the above tube, the annealing reaction was carried out (after heating at 95° C. for 5 minutes, the reaction mixture was cooled down at room temperature in 1.5 hours). Subsequently, 40 units of T4 ligase (manufactured by Boehringer) was added to the reaction solution, followed by incubation overnight at 12° C. After heating the reaction mixture at 68° C. for 10 minutes to inactivate the ligase, 20 µl of the solution was taken out, which was then subjected to the PCR using PCR primers on the 5'-end and the 3'-end of the RNase III (the netted part in FIG. 14). The PCR was carried out by using the DNA thermal cycler (model PJ 280, manufactured by Parkin-Elmer). The reaction conditions were 1 minute at 94° C., 2 minutes at 57° C., 2 minutes at 72° C., and 35 cycles of amplificataions were carried out. The PCR product was digested with EcoRI and SalI, followed by electrophoresing on 1.5% agarose gel. The 700 bp DNA fragment(RNase III gene) was purified from the gel and then cloned into the pBlue-script IISK+ (manufactured by Stratagene) vector.

The cloned RNase III gene DNA was confirmed to be identical with the DNA sequencing that had been designed in FIG. 14.

The RNase III gene DNA obtained here is capable of producing a plant showing resistance to plural viruses by ligating the DNA to the pBI121 plasmid to transfect into a plant.

EXAMPLE 9

Resistance against viruses in R1 plants (plants germinated from the seeds of a transgenic plant)

Seeds obtained from the pacI transgenic tobacco #8 (Xanthi nc) were placed in a hormone-free MS medium containing 500 µg/ml kanamycin, followed by selecting normally germinated kanamycin-resistant seedlings. These seedlings were propagated in vitro in a hormone-free MS medium containing no kanamycin, followed by extraction of DNA from the leaves (Ishida & Misawa, 1992, "Introduction to Experimental Manipulation in Cell Technology", Kodansha). After digesting the extracted DNA with restriction enzymes EcoRI and BamHI, the digested DNA was electrophoresed on 1% agarose gel and then subjected to Southern blotting. With the actin gene as an internal standard, the one having one copy of the pacI gene (hetero) as same as the R0 plant (the original pacI #8 Xanthi nc) and the one having two copies of the pacI gene (homo) were identified. R1 plants Xanthi nc #8-2 and #8-4 (homo), #8-3 (hetero) and a control (Xanthi nc tobacco) were subjected to an experiment of TMV inoculation. The TMV (the OM strain) was diluted to 0.1 µg/ml with a 10 mM phosphate buffer (pH 7.4) and then inoculated on the upper surface of the leaves of the above plants with carborundum as a abrasive. On the 4th day after inoculation, the number and the size of necrotic local lesions were observed (FIG. 16). From these results, it was confirmed that the virus-resistant character of a plant transformed with the pacI gene was transmitted to R1 progenies.

INDUSTRIAL APPLICABILITY

A plant expressing the double-strand RNase (the pacI gene product) had resistance to TMV, CMV, etc. These viruses are plant viruses belonging to different taxonomic groups and are greatly different from each other in various respects such as genome structure, gene expression mode, mechanism of replication, etc. For example, the TMV is a monopartite virus carrying a single genome RNA, whereas the CMV is a tripartite virus carrying a three-segmented geneome RNA. A case, in which a recombinant plant showing resistance to plural viruses which are greatly different from each other as above is produced by transformation and expression of a single gene, has not been known at all so far.

Showing resistance to both TMV and CMV which are quite different from each other in replication mechanism means that the replication of a wide range of RNA viruses is suppressed by the expression of the double-strand RNase and the multiplication of the viruses is inhibited. In addition, any virus including mutated one needs to form a double-strand RNA in its replication stage as far as it is a RNA virus. Therefore, it can be said to be obvious for those skilled in the art that the possibility of the appearance of an overcomer virus which overcomes the virus resistance owing to the expression of the double-strand RNase is extremely low.

As described above, it is considered that the present techniques for producing virus-resistant plant by genetic recombination can be widely applied to the breeding of virus-resistant plant varieties.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 709 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:1:

| | | | | | | |
|---|---|---|---|---|---|---|
| CCGAATTCCA | TGAACCCAAT | CGTTATCAAC | AGGCTTCAAA | GGAAGCTTGG | ATACACCTTC | 60 |
| AACCACCAAG | AGCTTCTTCA | ACAAGCTCTT | ACCCACAGGT | CTGCTTCTTC | TAAGCACAAC | 120 |
| GAGAGGCTTG | AGTTCCTTGG | AGACTCTATC | CTTTCTTACG | TTATCGCTAA | CGCTCTTTAC | 180 |
| CACAGGTTCC | CAAGGGTTGA | CGAGGGAGAC | ATGTCTAGGA | TGAGGGCTAC | CCTTGTTAGG | 240 |
| GGAAACACCC | TTGCTGAGCT | TGCTAGGGAG | TTCGAGCTTG | GAGAGTGCCT | TAGGCTTGGA | 300 |
| CCAGGAGAGC | TTAAGTCTGG | AGGATTCAGG | AGGGAGTCTA | TCCTTGCTGA | CACCGTTGAG | 360 |
| GCTCTTATCG | GAGGAGTTTT | CCTTGACTCT | GACATCCAAA | CCGTTGAGAA | GCTTATCCTT | 420 |
| AACTGGTACC | AAACCAGGCT | TGACGAGATC | TCTCCAGGAG | ACAAGCAAAA | GGACCCAAAG | 480 |
| ACCAGGCTTC | AAGAGTACCT | TCAAGGAAGG | CACCTTCCAC | TTCCAACCTA | CCTTGTTGTT | 540 |
| CAAGTTAGGG | GAGAGGCTCA | CGACCAAGAG | TTCACCATCC | ACTGCCAAGT | TTCTGGACTT | 600 |
| TCTGAGCCAG | TTGTTGGAAC | CGGATCTTCT | AGGAGGAAGG | CTGAGCAAGC | TGCTGCTGAA | 660 |
| CAAGCTCTTA | AGAAGCTTGA | GCTTGAATAA | TTTTAGCAG | AGTCGACGG | | 709 |

What is claimed is:

1. A method for producing a plant having resistance against RNA viruses, comprising integrating a DNA sequence, which encodes a protein having an enzyme activity that specifically cleaves a double-strand RNA, into a chromosome of a plant and making the DNA sequence express in the plant cells.

2. A method according to claim 1, wherein said protein having an enzyme activity that specifically cleaves a double-strand RNA is ribonuclease III derived from *Escherichia coli* or a pacI gene derived from yeast.

3. A plant having resistance to RNA viruses, in which a heterologous DNA sequence, which encodes a protein having an enzyme activity that specifically cleaves a double-strand RNA, is integrated into its chromosome and expressed therein.

4. A plant according to claim 3, wherein said protein having an enzyme activity that specifically cleaves a double-strand RNA is ribonuclease III derived from *Escherichia coli* or a ribonuclease encoded in a pacI gene derived from yeast.

5. A method according to claim 1, wherein said protein having an enzyme activity that specifically cleaves a double-strand RNA is a ribonuclease encoded by a pacI gene derived from yeast.

6. A method according to claim 1, wherein said RNA virus is selected from the group consisting of tobacco mosaic virus, cucumber mosaic virus and potato virus Y.

7. A method according to claim 1, wherein said plant is a tobacco plant.

8. A method according to claim 1, wherein said protein having an enzyme activity that specifically cleaves a double-strand RNA is a ribonuclease encoded by a pacI gene derived from yeast, said RNA virus is selected from the group consisting of tobacco mosaic virus, cucumber mosaic virus and potato virus Y and said plant is a tobacco plant.

9. A plant according to claim 3, wherein said protein having an enzyme activity that specifically cleaves a double-strand RNA is a ribonuclease encoded by a pacI gene derived from yeast.

10. A plant according to claim 3, wherein said RNA virus is selected from the group consisting of tobacco mosaic virus, cucumber virus and potato virus Y.

11. A plant according to claim 3, wherein said plant is a tobacco plant.

12. A plant according to claim 3, wherein said protein having an enzyme activity that specifically cleaves a double-strand RNA is a ribonuclease encoded by a pacI gene derived from yeast, said RNA virus is selected from the group consisting of tobacco mosaic virus, cucumber mosaic virus and potato virus Y, and said plant is a tobacco plant.

* * * * *